(12) United States Patent
Kent et al.

(10) Patent No.: US 11,607,208 B2
(45) Date of Patent: Mar. 21, 2023

(54) TISSUE SECURING DEVICE AND METHOD OF USE

(71) Applicants: Joshua Gilbert Kent, Rexford, NY (US); Trevor Anthony Grigas, Schenectady, NY (US); Alec Zierer, Niskayuna, NY (US)

(72) Inventors: Joshua Gilbert Kent, Rexford, NY (US); Trevor Anthony Grigas, Schenectady, NY (US); Alec Zierer, Niskayuna, NY (US)

( * ) Notice: Subject to any disclaimer, the term of this patent is extended or adjusted under 35 U.S.C. 154(b) by 643 days.

(21) Appl. No.: 16/536,865

(22) Filed: Aug. 9, 2019

(65) Prior Publication Data

US 2020/0069301 A1 Mar. 5, 2020

Related U.S. Application Data

(60) Provisional application No. 62/716,641, filed on Aug. 9, 2018.

(51) Int. Cl.
*A61B 17/02* (2006.01)
*A61B 17/00* (2006.01)
(Continued)

(52) U.S. Cl.
CPC ...... *A61B 17/0218* (2013.01); *A61B 17/0231* (2013.01); *A61B 17/0206* (2013.01);
(Continued)

(58) Field of Classification Search
CPC . A61B 17/0218; A61B 17/02; A61B 17/0231; A61B 17/0206; A61B 17/025; A61B 17/28; A61B 17/2812; A61B 17/2816; A61B 17/282; A61B 17/2833; A61B 17/2841; A61B 17/29; A61B 17/2909; A61B 2017/2837; A61B 2017/2808; A61B 2017/2901; A61B 2017/2904; A61B 2017/2905; A61B 2017/2926; A61B 2017/2938; A61B 2017/2946; A61B 2017/2947; A61B 2090/032
(Continued)

(56) References Cited

U.S. PATENT DOCUMENTS 4,034,746 A * 7/1977 Williams ........... A61B 17/0206
600/217
4,867,139 A * 9/1989 Girzadas ................ A61B 17/02
606/86 R (Continued)

*Primary Examiner* — Marcela I. Shirsat

(57) ABSTRACT

This disclosure relates to a medical device. The medical device comprises a first and a second component. The first component comprises a first portion having a first handle part and a second portion having a grip. The second component is linked to the first component and is configured to be in communication with the first component to be actuated from an open to a closed position. The second component defines a third portion and a fourth portion, the third portion defining a second handle part and the fourth portion defining a second grip that is configured to grip a tissue in combination with the first grip portion of the first component. In certain embodiments, the first component or second component comprises a substantially straight member attached distally from the grip.

4 Claims, 8 Drawing Sheets

(51) Int. Cl.
  *A61B 17/29*  (2006.01)
  *A61B 17/28*  (2006.01)
  *A61B 90/00*  (2016.01)

(52) U.S. Cl.
  CPC ......... *A61B 17/282* (2013.01); *A61B 17/2816* (2013.01); *A61B 17/2909* (2013.01); *A61B 2017/00477* (2013.01); *A61B 2017/00951* (2013.01); *A61B 2017/00955* (2013.01); *A61B 2017/2837* (2013.01); *A61B 2017/2926* (2013.01); *A61B 2090/032* (2016.02)

(58) Field of Classification Search
  USPC ........................................ 600/218, 235, 236
  See application file for complete search history.

(56) References Cited

U.S. PATENT DOCUMENTS

| | | | |
|---|---|---|---|
| 6,375,611 B1* | 4/2002 | Voss ....................... | A61B 17/02 600/210 |
| 2015/0305762 A1* | 10/2015 | Dunn ..................... | A61B 17/30 606/205 |
| 2017/0042524 A1* | 2/2017 | Angus ................ | A61B 17/0218 |
| 2018/0353164 A1* | 12/2018 | Laird, Jr. ........... | A61B 17/0206 |
| 2020/0146665 A1* | 5/2020 | Costantini .......... | A61B 17/0218 |

\* cited by examiner

TISSUE SECURING DEVICE AND METHOD OF USE

FIELD

The disclosed methods and systems relate to the medical field, and more particularly to medical procedures.

BACKGROUND

Medical practitioners are presented with thousands of emergency room admissions every year relating to injuries sustained through foreign materials becoming lodged in tissues. The eye is particularly susceptible to damage through materials coming into contact with the surface of the eye. In many instances, these materials can become lodged in areas underneath eyelids. When foreign materials become lodged between the eyelid and the cornea or sclera, these materials must be removed to prevent permanent injuries.

The devices and techniques known in the prior art for allowing for extraction of foreign materials from difficult areas of the body have several issues that impact patient comfort, treatment efficacy, and prognosis. For instance, the present methods of extracting foreign materials from areas such as the eye consist of swabs in combination with an inspection mirror to hold the eyelid away from the eye. This technique causes substantial discomfort to the patient, and in some instances requires anesthesia, while making extraction of the foreign materials from the eye more difficult. Other techniques include holding back or cutting blocking tissues or attempting to wash out the foreign materials. All of these techniques present medical practitioners with a difficult task and patients with discomfort and potential tissues damage.

These issues remain unresolved and require addressing to improve patient treatment outcomes.

SUMMARY

The present disclosure relates to a device that allows for a medical professional to move a first tissue out of the way of a second tissue requiring treatment and to hold the first tissue securely out of the way of the second tissue during a procedure. The device further allows the medical professional to effectively remove foreign materials from the second tissue, or from between the two tissues, while not needing to cut or permanently remove the first tissue out of the way of the second tissue. In certain embodiments, the first tissue is an eyelid and a second tissue is the surface of an eye. In some embodiments, the medical professional can secure the tissue out of the way with one hand and with the second hand use a second medical device, such as a swab or other device, to remove the foreign materials.

Aspects of the disclosed devices comprise a first component comprising a first portion that defines a first handle part and a second portion that defines a first grip that is configured to grip a tissue in combination with a second grip. The second component is linked to the first component and is configured to be in communication with the first component to be actuated from an open to a closed position. The second component defines a third portion and a fourth portion, the third portion defining a second handle part and the fourth portion defining a second grip that is configured to grip a tissue in combination with the first grip portion of the first component. In certain embodiments, the gripping portions of both the first and second components are curved and contain the same radii. In certain embodiments, the first component or second component comprises a substantially straight member attached distally from the grip. In some embodiments, the member is configured to be gripped between two fingers. In other embodiments, the member is positioned parallel to the plane of the component. In yet other embodiments, the member is positioned at an angle of 5° to 90° to the plane of the component.

Aspects disclosed herein include methods of using the disclosed devices. The method comprises actuating the device from an open position to a closed position to grip a first tissue. The method further comprises moving the first tissue to a position that exposes a second tissue, by moving the device in either a rotational or translational motion, and holding a substantially straight member connected to a first component of the device to maintain the first tissue in the position that exposes the second tissue. The method can further comprise treating a second tissue that has been exposed.

Aspects of the device comprise a first component and a second component, the first component comprises a first portion and a second portion, the first portion defining a first handle part and the second portion defining a first grip configured to grip a tissue in combination with a second grip, wherein the second component is linked to the first component and is configured to be in communication with the first component to be actuated from an open configuration to a closed configuration and wherein the second component defines a third portion and a fourth portion, the third portion defining a second handle part and the fourth portion defining a second grip that is configured to grip a tissue in combination with the first grip portion of the first component, and wherein the device comprises a member attached to the first or second component.

In certain embodiments, the member is substantially straight. In other embodiments, the member is perpendicular to a plane of the first or second component to which the member is attached. In still other embodiments, the member is attached at an angle of 50 degrees to 110 degrees when compared to a plane of the first or second component to which the member is attached. In further embodiments, the member is comprised of the same material as the first or second component.

In certain embodiments, the member and the first or second component to which the member is attached are shaped from a single material. In particular embodiments, the member is from about 2.0 cm to about 10 cm. In more particular embodiments, the member further comprises a coating. In still more particular embodiments, the coating is a polymer or film. In yet more particular embodiments, the coating comprises plastic, biocompatible adhesive polymers, and rubber polymers. In even more particular embodiments, the coating is a sheath.

In some embodiment, the first and second component comprise a coating on the first and second grips. In other embodiments, the coating is a polymer or film. In yet other embodiments, the coating comprises plastic, biocompatible adhesive polymers, and rubber polymers. In further embodiments, the coating is a sheath.

In certain embodiments, the member is disposed proximally to the first or second grip of the first or second component to which the member is attached. In some embodiments, the member is disposed on the first or second grip of the first or second component to which the member is attached. In more embodiments, the member is disposed on opposite side of the first or second grip of the first or second component to which the member is attached, the opposite side opposing the side of the first or second grip that comes together with the opposing side of the other grip to hold the tissue. In still more embodiments, the first and second grips are substantially elliptical. In still further embodiments, the first and second grips contact one another at the apex of the ellipse when in a closed state. In even further embodiments, the device further comprises a locking mechanism.

In particular embodiments, the locking mechanism comprises two lock components, the first lock component being disposed on the first portion and the second lock component being disposed on the second portion. In even more particular embodiments, the first and second lock components are configured to interlock with one another. In yet more particular embodiments, the first and second lock components comprise interlocking teeth such that the interlocking teeth on each component lock with one another. In still more particular embodiments, the locking mechanism prevents actuation of the first and second portions into an open configuration.

In certain embodiments, the device comprises a first material selected from the group consisting of thermoplastics, alloys, gold, aluminum, tantalum, and combinations thereof. In particular embodiments, the device comprises a thermoplastic.

Aspects of the disclosure include a method of displacing a tissue from a first position to a second position. The method comprises providing a device comprising a first component and a second component, the first component comprises a first portion and a second portion, the first portion defining a first handle part and the second portion defining a first grip configured to grip a tissue in combination with a second grip, wherein the second component is linked to the first component and is configured to be in communication with the first component to be actuated from an open configuration to a closed configuration and wherein the second component defines a third portion and a fourth portion, the third portion defining a second handle part and the fourth portion defining a second grip that is configured to grip a tissue in combination with the first grip portion of the first component, and wherein the device comprises a member attached to the first or second component; gripping the tissue with the device by actuating the first and second components into a closed configuration onto the tissue; moving the tissue from the first position to the second position by pulling the tissue into the second position; and maintaining the tissue in the second position, a user maintaining the tissue by holding the member.

In certain embodiments, the tissue is skin, organ, tendon, ligament, muscle, or combinations thereof. In other embodiments, the tissue is an eyelid. In still other embodiments, the method further comprises cleansing a body structure of foreign material.

In certain embodiments, the member is substantially straight. In other embodiments, the member is perpendicular to a plane of the first or second component to which the member is attached. In still other embodiments, the member is attached at an angle of 50 degrees to 110 degrees when compared to a plane of the first or second component to which the member is attached. In further embodiments, the member is comprised of the same material as the first or second component.

In certain embodiments, the member and the first or second component to which the member is attached are shaped from a single material. In particular embodiments, the member is from about 2.0 cm to about 10 cm. In more particular embodiments, the member further comprises a coating. In still more particular embodiments, the coating is a polymer or film. In yet more particular embodiments, the coating comprises plastic, biocompatible adhesive polymers, and rubber polymers. In even more particular embodiments, the coating is a sheath.

In some embodiment, the first and second component comprise a coating on the first and second grips. In other embodiments, the coating is a polymer or film. In yet other embodiments, the coating comprises plastic, biocompatible adhesive polymers, and rubber polymers. In further embodiments, the coating is a sheath.

In certain embodiments, the member is disposed proximally to the first or second grip of the first or second component to which the member is attached. In some embodiments, the member is disposed on the first or second grip of the first or second component to which the member is attached. In more embodiments, the member is disposed on the opposite side of the first or second grip of the first or second component to which the member is attached, the opposite side opposing the side of the first or second grip that comes together with the opposing side of the other grip to hold the tissue. In still more embodiments, the first and second grips are substantially elliptical. In still further embodiments, the first and second grips contact one another at the apex of the ellipse when in a closed state. In even further embodiments, the device further comprises a locking mechanism.

In particular embodiments, the locking mechanism comprises two lock components, the first lock component being disposed on the first portion and the second lock component being disposed on the second portion. In even more particular embodiments, the first and second lock components are configured to interlock with one another. In yet more particular embodiments, the first and second lock components comprise interlocking teeth such that the interlocking teeth on each component lock with one another. In still more particular embodiments, the locking mechanism prevents actuation of the first and second portions into an open configuration.

In certain embodiments, the device comprises a first material selected from the group consisting of thermoplastics, alloys, gold, aluminum, tantalum, and combinations thereof. In particular embodiments, the device comprises a thermoplastic.

DETAILED DESCRIPTION

The disclosed devices allow for medical professionals to move a first tissue that is blocking, covering, or otherwise obstructing a second tissue requiring treatment into a position allowing treatment of the second tissue. The disclosed devices further allow for medical professionals to treat patients in the most efficient and efficacious manner. The disclosed devices also allow for multiple practitioners to operate in a confined space. For example, one practitioner can hold the device to maintain the first tissue in a position away from the second tissue, while another practitioner performs a procedure on the second tissue. The first tissue can be an eyelid and the second tissue can be the surface of the eye, in some embodiments.

Figure 1:
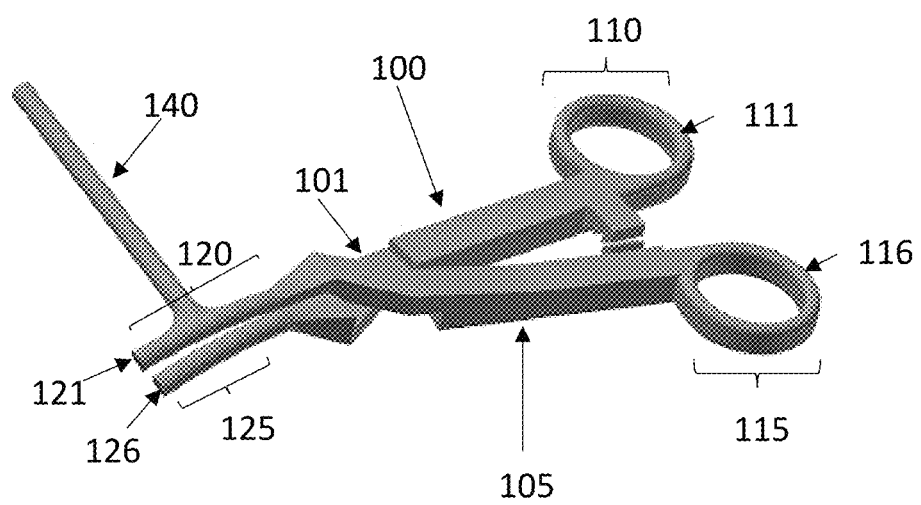
FIG. 1 is a representation of an exemplary embodiment of a device.

As shown in FIG. 1, an exemplary embodiment comprises a first component 100 and a second component 105. The first component 100 and the second component 105 are configured to be linked together to be actuated from an open position to a closed position. The first component 100 and second component 105 each have a portion that allows for interlocking of the first and second components to actuate, a linking position 101. Actuation in this instance includes moving the first component grip portion 121 and second component grip portion 126 to an open position (i.e., away from one another) and to a closed position (i.e., in contact with one another). This actuation allows a practitioner to grip (closed position) and release (open position) tissue.

FIG. 1 further shows that the first component 100 comprises a first portion 110 and a second portion 120. The first portion 110 of the first component defines a first handle part 111 and the second portion 120 of the first component 100 defines a first grip 121 configured to grip a tissue in combination with a second grip. The second component 105 is linked to the first component and is configured to be in communication with the first component to be actuated from an open to a closed position. The second component 105 defines a third portion 115 and a fourth portion 125. The third 115 and fourth portions 125 can be substantially identical to the first 110 and second portions 120 of the first component 100, respectively. For instance, the third portion 115 defines a second handle part 116 and the fourth portion 125 defines a second grip 126 that is configured to grip a tissue in combination with the first grip portion 121 of the first component 100.

The disclosed devices can further comprise a substantially straight member 140. As shown in FIG. 1, the member 140 is located on the first component 100. However, it should be noted that the member 140 can be located on either the first component 100 or the second component 105. In some embodiments, the member 140 is located distally from the end of the grip on either the first 100 or second component 105. The member 140 can be positioned parallel to a plane of the component or alternatively positioned at an angle from the plane of the component. For example, the member can be positioned from 5° to 90° from the plane of the component. In some embodiments, the member 140 comprises a textured surface to allow for gripping of the member 140.

The first component 100 and second component 105 each comprise a grip (121 and 126) in the second portion 120 and fourth portions 125, respectively. The grips 121 and 126 are configured to contact one another in the closed position of the disclosed devices. The grip portions 121 and 126 contact a first tissue and grip it securely. The grips can be smooth or serrated.

Figure 3A:
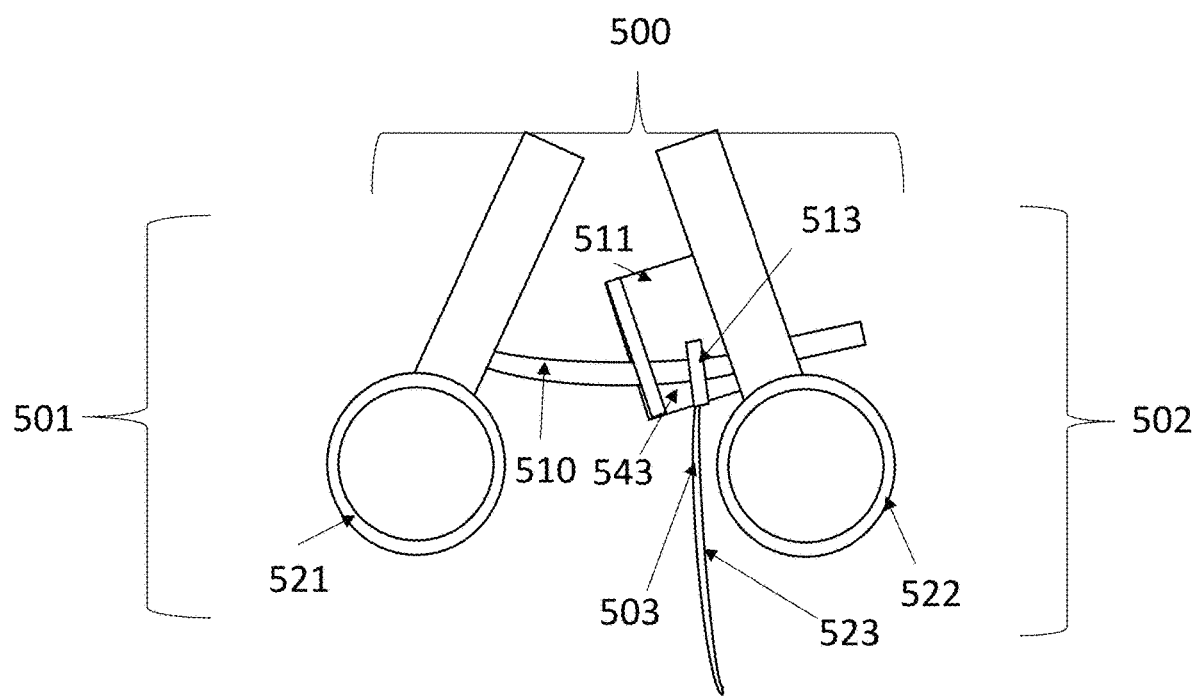
FIG. 3a is a representation of an exemplary locking mechanism between the first and second components of a device.
Figure 3B:
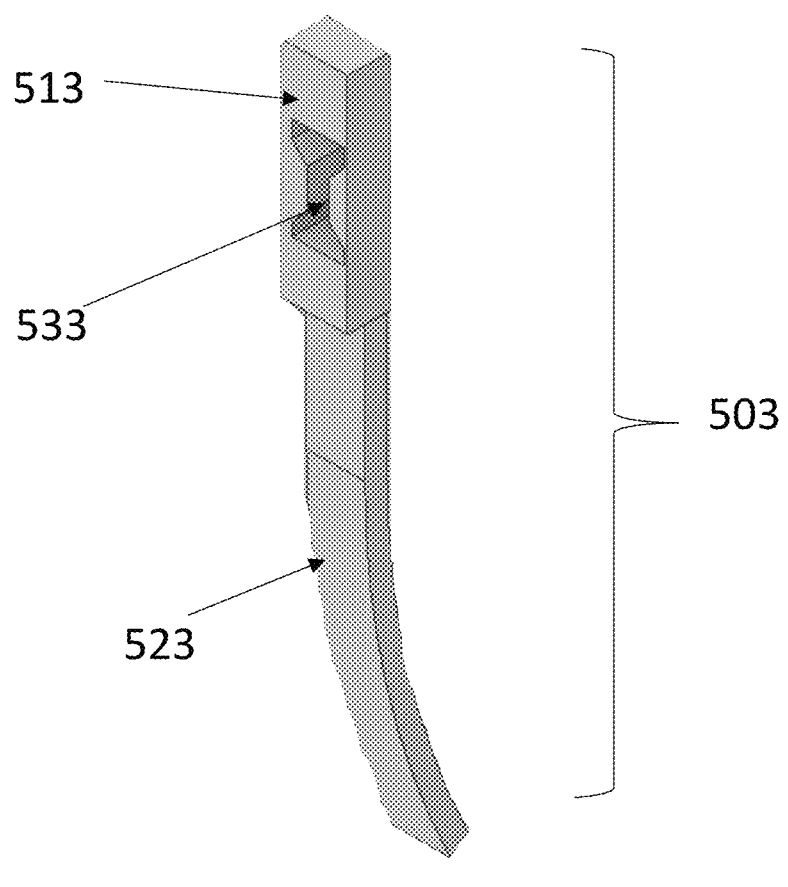
FIG. 3b is a representation of a third component of the locking mechanism in close-up view.

In FIG. 3a, an embodiment of the locking mechanism 500 is shown. In this embodiment, the locking mechanism 500 comprises an extended arm 510 extending from the first component 501 to the second component 502 near the first handle part 521 and the second handle part 522. In the embodiment of FIG. 3a, the extended arm 510 is molded to the first component 501. However, the extended arm 510 can be attached as a separate piece to the first component 501 through adhesion, welding, or other known techniques. FIG. 3a further shows an extended compartment 511 connected to the second component 502. The extended arm 510 passes through the compartment 511, and then through the second component 502 and a third component 503. This third component 503 is comprised of a first portion 513 and second portion 523 (see FIG. 3b). The first portion 513 of the third component 503 defines a slot 533 for the extended arm 510 to pass through. The compartment 511 of the second component 502 defines an extended member 512. The third component 503 is held in a primary position, within the compartment 511 by a spring 504 and an extended member 512, so that it causes enough friction to stop the second component 502 and the compartment 511 from sliding along the extended arm 510. The third component 503 is then moved into a secondary position by applying force to the extended member 523 in the direction of the first component 501. A spring 504 resistance against the force. Once in this secondary position the third component 503 allows the second component 502 and its compartment 511 to move along the extended arm 510. The third component 503 can be held in these positions using various methods. Examples of these methods include springs and fixed pivot points within the compartment.

Figure 4:
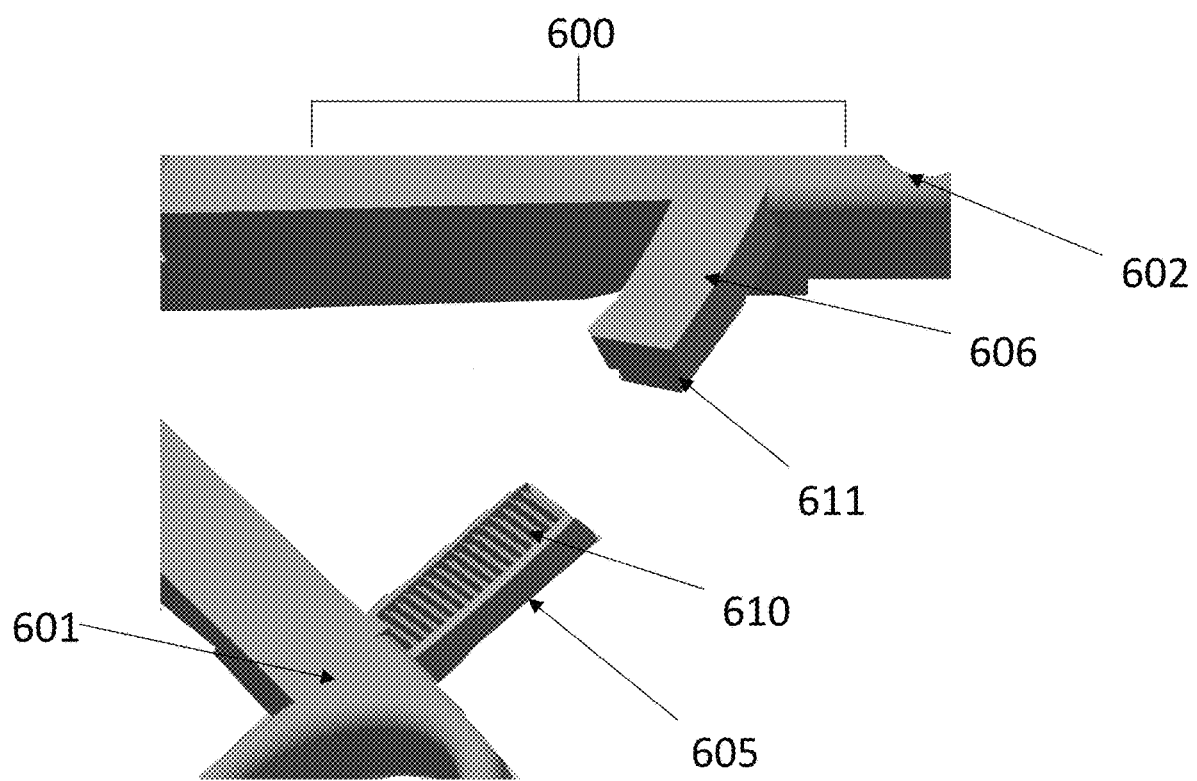
FIG. 4 is a representation of another embodiment of the locking mechanism.

FIG. 4 shows an alternative locking mechanism 600. The locking mechanism 600 can be positioned to interlock between the first handle part 601 and the second handle part 602. FIG. 4 further shows that the locking mechanism 600 comprises an extension 605 with interlocking teeth 610. There is a second extension 606 from the second handle part 602 that also has interlocking teeth 611. The interlocking teeth 610 are configured to interlock with the teeth 611 and thereby keep the mechanism 600 in a locked position. In this position, the interlocking teeth 610 prevent the device from being actuated to an open configuration. The locking mechanism 600 however can be a variety of configurations. Examples of locking mechanisms include latching mechanisms, lock-and-key mechanisms, and other mechanisms to hold the first and second handle parts in a closed position.

In some embodiments, the gripping portions comprise gel material. The gel material can be compressible to absorb force. The gel material can further be biocompatible. Examples of gel materials include silicone gel such as POWERSIL® GEL C 670 AB (Wacker Chemie AG), hydrogel, organogel, and nanocomposite hydrogel. The gel material can coat the gripping portion. In some embodiments, the gel material is a filler of a flexible polymer. The flexible polymer can be attached to the gripping portion that contacts the tissue when the gripping portions grip the tissues.

Figure 5:
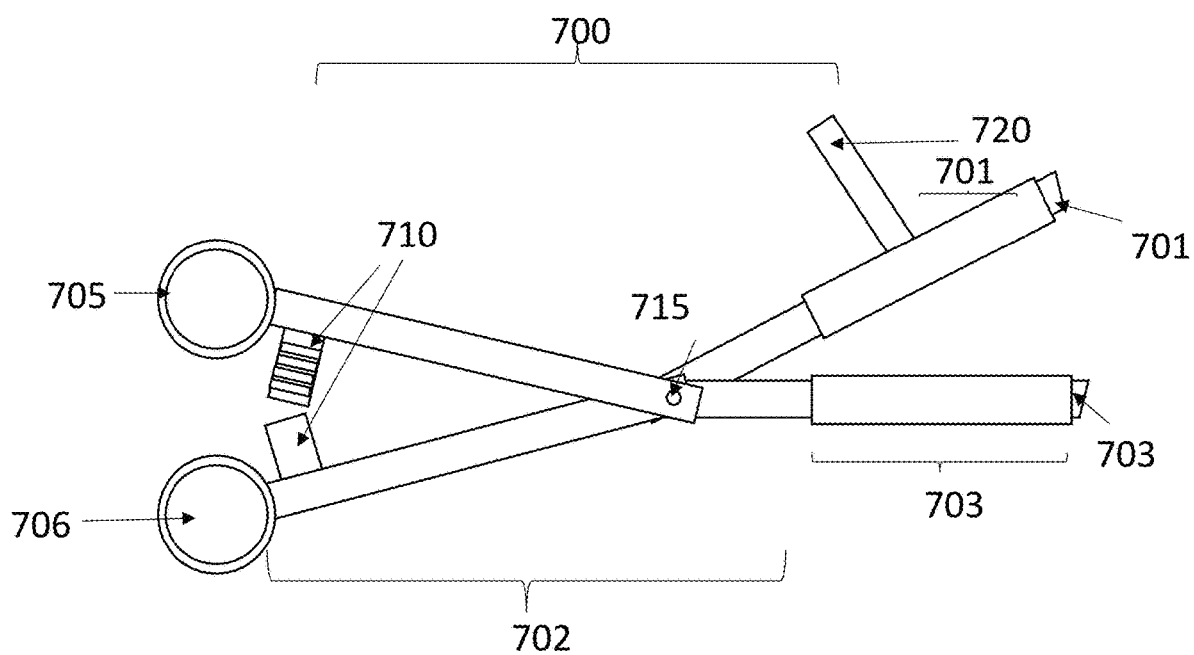
FIG. 5 is a designed model of an exemplary embodiment of the device.

Embodiments of the disclosed devices include devices as shown in FIG. 5. The first 701 and second 703 gripping portions of the first 700 and second components 702, respectively. The gripping portions 701 and 703 in this embodiment are designed to close in parallel fashion. In this embodiment, the griping portions are coated with a protective sleeve 701a and 703a. As shown, the device comprises a locking mechanism 710 and a first handle part 705 and a second handle part 706. The linking position 715 is also shown as well as member 720. The sleeve can be a gel or material that protects tissue from crush damage.

In certain embodiments, the disclosed devices are composed of a first material selected from the group consisting of thermoplastics, alloys, gold, aluminum, tantalum, and combinations thereof. In particular embodiments, the disclosed devices are composed of thermoplastics.

In further embodiments, the disclosed devices comprise a surface coating the grip of the first and second components. The surface coating can be used to improve gripping of tissues and to decrease the chance of crush damage to tissues. The surface coating can be a material that increases friction to allow for a more secure hold while reducing the amount of stress imposed on the tissue that is being secured. For instance, the surface coating can increase the grip of the tissue without the need for crushing force. The surface coating can comprise a polymer or film that is disposed on the grip. Examples of such materials include plastic, biocompatible adhesive polymers, and natural or synthetic rubber polymers. The surface coating can also be a separate sheath that one can slide onto the grip of each of the first and second components. For example, a rubber sheath can be made that is a hollow tube that fits securely onto the grip portion.

In some embodiments, the disclosed devices comprise first and second components in which the respective grip portions comprise a groove. The groove extends at least part of the length of the grip and is configured to hold an insert. The insert improves the gripping of tissue and acts in a similar manner to the surface coatings disclosed herein. The insert can comprise a material such as plastic, natural and synthetic rubber, biocompatible adhesive polymers, or combinations thereof. The insert can be secured in the groove by an adhesive. In certain embodiments, the insert is not secured in the groove but is fitted into the groove.

Figure 2A:
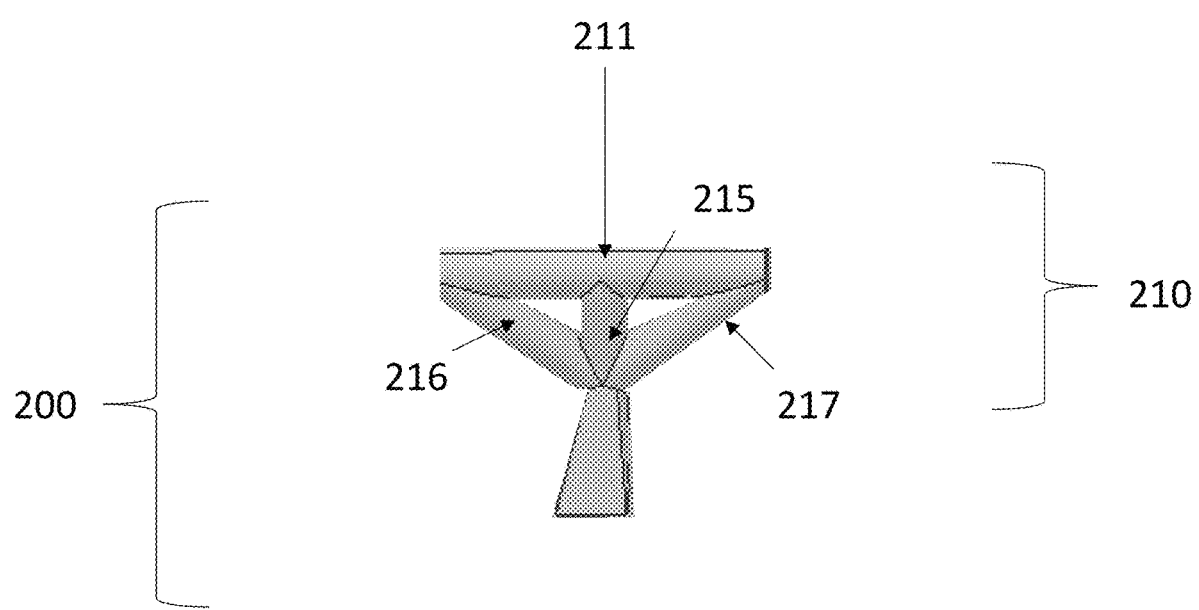
FIG. 2a is a top view of an exemplary embodiment showing the grip portion of the device.

FIG. 2a shows an embodiment of the device in which the first and second components comprise a first grip 200 and a second grip. FIG. 2a being a top portion shows first grip 210 of the first component 200 and in this embodiment the second grip is identical to the first grip 200. The first grip 200 and, therefore, the second grip in this embodiment, comprises a first section 211 of the first grip 210 that grip the tissue in combination with the second grip. The first grip 211 comprises three supports 215, 216, and 217. A first support 215 is positioned substantially in the middle of the first grip 210. The second 216 and third supports 217 are positioned at opposite ends of the first section 211 of the first grip 210. This can also be replaced by a single support that spans the same area as 215, 216, 217.

Figure 2B:
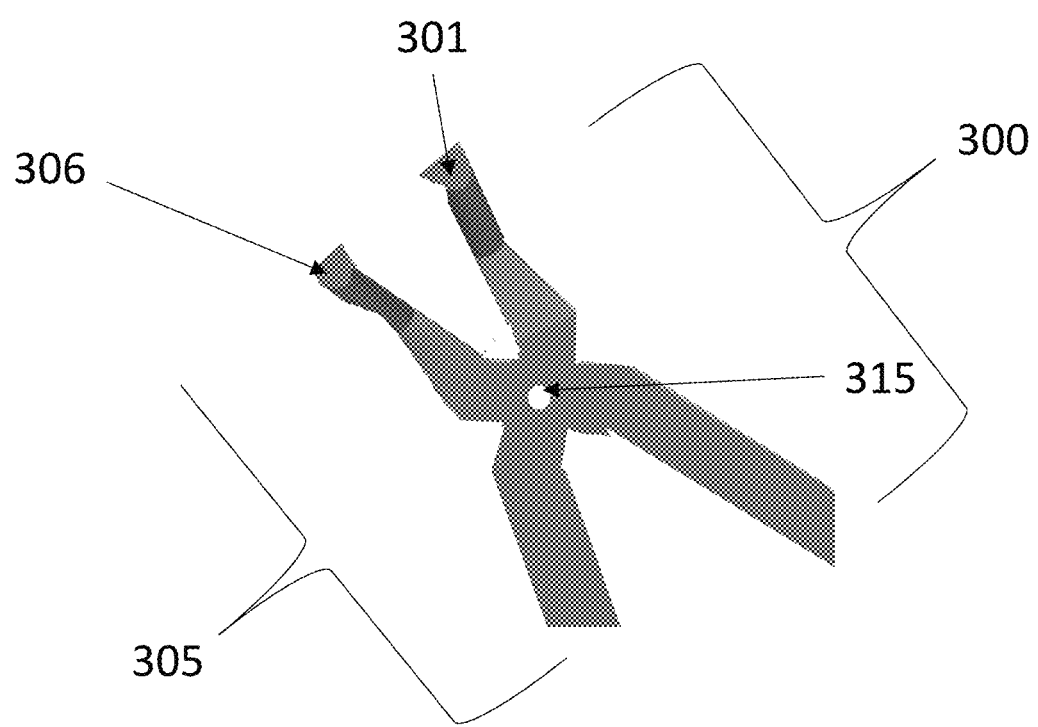
FIG. 2b is a side view of an exemplary embodiment showing the grip portion.

FIG. 2b shows embodiments of the device in which the device comprises a first component 300 and a second component 305. The first 300 and second components 305 comprise first 301 and second grips 306, respectively. The first 300 and second components 305 are linked at a linking position 315. It should be noted that this is a sideview in which the supports shown in FIG. 2a are not visible at this angle. The first 301 and second grips 306 are shaped as substantially elliptical. As shown in FIG. 2b, the first 301 and second grips 306 make contact at the apex of the ellipses to grip the tissues.

Figure 2C:
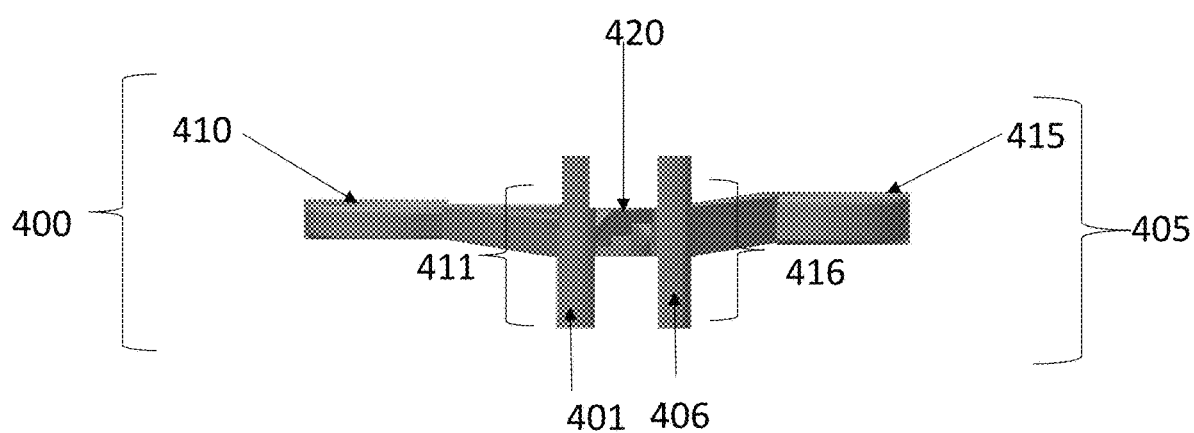
FIG. 2c is a front view of an exemplary embodiment showing the grip portion.

FIG. 2c shows embodiments of the device in which the first 401 and second grips 406 have a perpendicular surface that makes contact to grip the tissues. FIG. 2c is a head-on view of the first component 400 and the second component 405 showing the linking position 420, as well as the first handle part 410 and the second handle part 415 in relation to one another in an open configuration of the device. This view shows the first section 411 of the first grip 401 and the second section 416 of the second grip 406. The first section 411 and the second section 416 each include the supports described in FIG. 2a.

Aspects disclosed herein include methods using the disclosed devices. The method comprises actuating the device from an open position to a closed position to grip a first tissue. The method further comprises moving the first tissue to a position that exposes a second tissue, by moving the device in either a rotational or translational motion, and holding a substantially straight member connected to a first component of the device to maintain the first tissue in the position that exposes the second tissue. The method can further comprise treating a second tissue that has been exposed.

As disclosed herein, the disclosed methods provide for the ability of medical practitioners to displace tissues during medical procedures. Exemplary medical procedures include removing debris from a tissue or organ, plastic surgery, surgical procedures on a tissue, and removing diseased tissues from organs. In certain embodiments, the medical procedure is removing foreign objects from a tissue or organ. In particular embodiments, the medical procedure is removing foreign objects from an eye. In more particular embodiments, an eyelid is gripped and moved out of the way to allow from access to the eyeball and removal of foreign objects.

Aspects of the methods disclosed herein include a method of displacing a tissue from a first position to a second position. The method comprises providing a device comprising a first component and a second component, the first component comprises a first portion and a second portion, the first portion defining a first handle part and the second portion defining a first grip configured to grip a tissue in combination with a second grip, wherein the second component is linked to the first component and is configured to be in communication with the first component to be actuated from an open configuration to a closed configuration and wherein the second component defines a third portion and a fourth portion, the third portion defining a second handle part and the fourth portion defining a second grip that is configured to grip a tissue in combination with the first grip portion of the first component, and wherein the device comprises a member attached to the first or second component; gripping the tissue with the device by actuating the first and second components into a closed configuration onto the tissue; moving the tissue from the first position to the second position by pulling the tissue into the second position; and maintaining the tissue in the second position, a user maintaining the tissue by holding the member.

It should be noted that the use of the term "a" or "an" means "one or more" throughout this application unless explicitly described otherwise. As used herein, the term "about" means+/−10% of the shown value that the term about modifies.

EQUIVALENTS

Those skilled in the art will recognize, or be able to ascertain, using no more than routine experimentation, numerous equivalents to the specific embodiments described specifically in this disclosure. Such equivalents are intended to be encompassed in the scope of the following claims.

We claim:

1. A device comprising a first component and a second component, the first component comprises a first portion and a second portion, the first portion defining the first handle part and the second portion defining the first grip configured to grip a tissue in combination with a second grip, wherein the second component is linked to the first component and is configured to be in communication with the first component to be actuated from an open configuration to a closed configuration and wherein the second component defines a third portion and a fourth portion, the third portion defining the second handle part and the fourth portion defining a second grip that is configured to grip a tissue in combination with the first grip portion of the first component, and wherein the device comprises a member attached to the first or second component, wherein the member is configured to allow a user to hold the member so as to allow a tissue to be secured in position, and wherein the member is disposed on, or proximally to, the first or second grip of the first or second component to which the member is attached and wherein the member is disposed on the first or second grip of the first or second component to which the member is attached, the member being disposed opposing the side of the first or second grip that comes together with the opposing side of the other grip to hold the tissue.

2. The device of claim 1, where the device further comprises a locking mechanism.

3. The device of claim 2, wherein the locking mechanism comprises two lock components, a first lock component being disposed on the first portion and a second lock component being disposed on the second portion, wherein the first and second lock components are configured to interlock with one another and prevent the actuation of the first and second portions into an open configuration.

4. The device of claim 3, wherein the first and second lock components comprise interlocking teeth such that the interlocking teeth on each component lock with one another.

* * * * *